Aug. 31, 1954 G. J. VON ABRAMS Plant Pat. 1,299
ROSE PLANT
Filed June 3, 1953
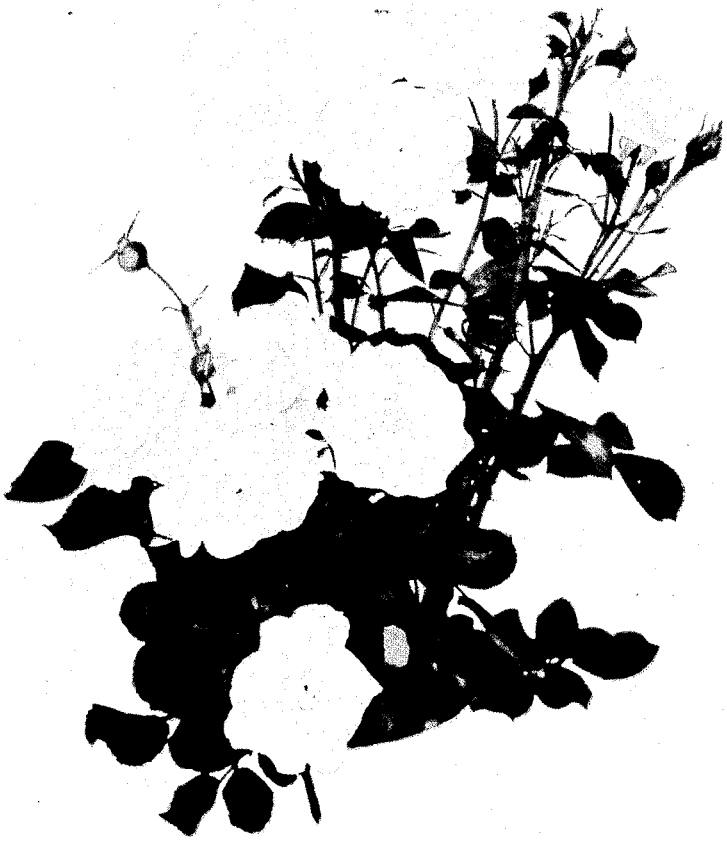
Inventor.
Gordon J. Von Abrams
By: Robb & Robb
Attorneys.

Patented Aug. 31, 1954

Plant Pat. 1,299

UNITED STATES PATENT OFFICE 1,299

ROSE PLANT

Gordon J. Von Abrams, Scappoose, Oreg., assignor to Eldon Pinkeney Dering, doing business under the trade name and style of Peterson & Dering, Scappoose, Oreg.

Application June 3, 1953, Serial No. 359,452

1 Claim. (Cl. 47—61)

The present invention relates to a new and distinct variety of rose plant which was originated by me by crossing the variety "Else Poulsen" (unpatented) with the variety "Fashion" (Plant Patent No. 789), the former being the seed parent, and the latter being the pollen parent. My new variety may be classed with the floribunda group of roses, although the pollen parent is not strictly a true polyantha hybrid.

The primary objective in making the foregoing cross was to obtain a refinement of the form and symmetry of the flower of the pollen parent, "Fashion," and to combine the same with the vigor, foliation and floriferousness that are characteristic of the seed parent "Else Poulsen." This objective was fully achieved, as evidenced by the fact that my new variety is phenotypically characterized as follows:

(1) A low-growing (2 to 3 feet), but vigorous and much-branched, compact bush;

(2) It flowers in a moderately large, closely packed cluster (cyme or compound cyme);

(3) The flowers are of unique form and color, and are distinct from any rose heretofore known to me in commerce;

(4) A heavy and continuous flowering habit throughout the growing season;

(5) An abundance and even distribution of foliage on the stems and branches; and (6) An unusual persistence of deep maroon color in the new foliage, generally imparting a distinct reddish cast to the growing plant.

In comparison with its parents, the new variety particularly differs therefrom in the following respects: With regard to the plant form of my new variety, it is less upright than that of "Else Poulsen" and somewhat more compact than that of "Fashion"; the young foliage of my new variety is darker than that of either parent, with a more persistent red coloration; the mature foliage of my new variety is also darker than that of either parent, but less elongate and not as heavy as that of "Else Poulsen"; the flower form of my new variety has a much more symmetrical petal pattern than that of "Fashion," and is much fuller than that of "Else Poulsen"; the petalage of the flowers of my new variety is characterized by many more petals than the flowers of "Else Poulsen," and several more than the flowers of "Fashion"; and the flower color of my new variety is easily distinguishable from that of either parent, and in particular, is less yellow than that of "Fashion."

Asexual reproduction of my new variety by budding at Scappoose, Oregon, shows that the foregoing characteristics and distinctions come true to form and are established and transmitted through succeeding propagations.

The accompanying drawing shows typical specimens of the flowers, foliage and stems of my new variety in different stages of development.

The following is a detailed description of my new variety, with color terminology in accordance with Robert F. Wilson's Horticultural Colour Chart, except where general color terms of ordinary dictionary significance are obvious:

Type: Outdoor bush; seedling; for outdoor decoration.

Class: Hybrid polyantha.

Breeding: Seedling.

*Seed parent.*—"Else Poulsen."

*Pollen parent.*—"Fashion."

Propagation: Holds its distinguishing characteristics through succeeding propagations by budding.

*Flower*

Locality where grown and observed: Scappoose, Oregon.

Flowers borne: Several to stem; in rounded cluster; on strong, short stems.

Quantity of bloom: Abundant, outdoors.

Continuity: Continuous.

Fragrance: Slight.

Bud:

*Peduncle.*—Medium length (4 to 5 cm.); medium heavy; erect; medium rough; with few red gland-tipped cilia. Color—near Scheele's Green, plate 360, page 175, heavily flushed or masked by a dark red, varying between extremes of Garnet Brown, Plate 00918, page 192, and Oxblood Red, Plate 00823, page 191.

*Before calyx breaks.*—Size—medium-small (1.3 x 1.2 cm.). Form—short-pointed; with foliaceous appendages on the margin of alternate sepals; without foliaceous parts extending beyond the tip of the bud. Color—near Scheele's Green, Plate 860/2, page 175 at base, flushed upward with near maroon, Plate 1030, page 185.

*As calyx breaks.*—Color—near Indian Lake, Plate 826/2, page 170, flushed with deep maroon, Plate 1030, page 185 (almost black).

*As first petal opens.*—Size—small (2 x 2½ cm.). Form—short-pointed. Color: outside—near Tyrian Rose, Plate 24, page 24; inside—from crimson, Plate 22, page 22, to Rose Madder, Plate 23, page 23.

*Opening.*—Opens well; is slightly retarded by cold, wet weather.

Bloom:

*Size (when fully open).*—Small (5 to 7 cm.).

*Petalage.*—Double (from 27 to 42 petals, but averaging 35 petals); arranged regularly.

*Form.*—Cupped at first; becoming open to imbricated; petals at first being slightly cupped, and becoming at maturity slightly rolled outward at the apex and along the apical lateral margins.

Petals:

*Texture.*—Medium thick; slightly soft; with inside velvety and outside satiny.

*Shape.*—Outside petal—obovate; generally entire, but sometimes with 2 obscure notches. Intermediate petal—obovate, generally entirely; sometimes with 2 obscure notches. Inside petal—obovate, generally entirely; sometimes with 2 obscure notches.

This description of a newly opened flower was made from a rose grown outdoors in the month of August, at Scappoose, Oregon:

*Color.*—On both sides of all petals, regardless of position, the basal tip is near white, with a Mimosa Yellow, Plate 602/2, page 143 flush above. Outer petal: outer surface—Tyrian Rose, Plate 24, page 24, shading to Rose Bengal, Plate 25/1, page 25 near base; inner surface—Tyrian Rose, Plate 24, page 24, shading to Rose Bengal, Plate 25, page 25 near base. Intermediate petal: outer surface—Tyrian Rose, plate 24/1, page 24, shading to Rose Bengal, Plate 25/1, page 25 near base; inner surface—Rose Madder, Plate 23/1, page 23, shading to Tyrian Rose, Plate 24/1, page 24 near base. Inner petal: outside surface—Tyrian Rose, Plate 24, page 24, shading to Tyrian Rose, Plate 24/1, page 24 near base; inner surface—Crimson, Plate 22/1, page 22.

This description was made from a rose that was open for 3 days in the month of August, at Scappoose, Oregon:

*Color.*—Basal tip near white as in newly opened flower. Outside petal: outside surface—Rose Bengal, Plate 25/1, page 25, shading to Rose Bengal, Plate 25/2, page 25 near base; inner surface—Tyrian Rose, Plate 24, page 24; where covered by overlapping petals, the color is much lighter, running to Tyrian Rose, Plate 24/3, page 24. Intermediate petal: outside surface—Rose Bengal, Plate 25/1, page 25; veins somewhat lighter and running to Rose Bengal, Plate 25/3, page 25; inner surface—Rose Madder, Plate 23/1, page 23; where surface is covered by adjacent petal, color becomes Tyrian Rose, Plate 24/3, page 24, or lighter. Inner petal: outside surface—from Tyrian Rose, Plate 24/1, page 24 to Tyrian Rose, Plate 24/2, page 24; inner surface—Rose Madder, Plate 23/1, page 23, shading to Rose Madder, Plate 23/2, or Plate 23/3, near base.

*General color effect.*—Newly opened flower—from Rose Madder, Plate 23/1, page 23 to Crimson, Plate 22/1, page 22. 3 days open—from Rose Madder, Plate 23/1, page 23 to Tyrian Rose, Plate 24/1, page 24.

*Behavior.*—Petals tend to persist; outer surfaces and areas not exposed (covered by overlapping petals) fade normally to lighter pink, but on surfaces exposed to strong sunlight, pigment appears to be concentrated in areas between veins, giving a stippled appearance; these markings are much darker than the petal color in any preceding stage and frequently as dark as Ruby Red, Plate 827/2, page 171, although there is much variation; the general color effect is therefore a darkening after maturity, followed by gradual fading; extremely hot, dry weather during senescence results in browning of the petals.

*Flower longevity.*—On outdoor bush—7 days in August. Grown outdoors and kept at living-room temperature—5 days in September.

*Reproductive organs*

Stamens: Moderately numerous (approximately 50); arranged regularly about pistils.

Filaments: Medium length (5 to 9 mm.); most with anthers. Color—near Primrose Yellow, Plate 601, page 65.

Anthers: Medium size; all open at nearly the same time. Color—near Yellow Ochre, Plate 07/1, page 101.

Pollen: Abundant. Color—varies from yellow to gold.

Pistils: Moderately numerous (approximately 40).

Styles: Even; medium length (7 to 10 mm.); medium diameter; loosely bunched. Color—near Carmine, Plate 21, page 21.

Stigma: Color—near Dresden Yellow, Plate 64/2, page 64.

Ovaries: All enclosed in calyx.

Hips: Short-obovoid to globular; moderately smooth; walls medium thick and fleshy. Color—near Scheele's Green, Plate 860/2, page 175.

Sepals: Persistent; moderate length (generally less than 2 cm.); spear-shaped; recurved. Color: inside—near Lavender Green, Plate 000761/1, page 196; outside—at base near Scheele's Green, Plate 860/1, page 175, heavily washed with Oxblood Red, Plate 00823, page 191.

Seeds: Usually many; medium size.

*Plant*

Foliage:

*Leaves.*—Compound of 5 to 7 leaflets, but usually 5; abundant; medium size; semi-glossy; heavy to leathery.

*Leaflets.*—Shape—ovate, with apex mucronate. Base—obtuse; sometimes slightly acute. Margins—simply serrate; some irregular double serration.

*Color.*—Mature: upper surface—darker tone of Nickel Green, Plate 57, page 57, or of Chrysocolla Green, Plate 56, page 56, but no corresponding exact color in Wilson's chart or any other; under surface—near a grayed darkened tone of Paris Green, Plate 58, page 58, but no exact color in Wilson's chart or any other. Young: upper surface—darker than Maroon, Plate 1030, page 185; nearly black; under surface—near Chrysanthemum Crimson, Plate 824/2, page 169, with all veins Maroon, Plate 1030, page 185, or darker; general color effect near Purple Madder, Plate 1028, page 181.

*Rachis.*—Medium size. Upper side—grooved; prickly; with few glandular cilia on margin. under side—sparsely thorny; very few glandular cilia.

*Stipules.*—Medium length; medium width; with medium length points turning out at an angle of less than 45°; sometimes recurved toward the stem.

*Disease.*—Better than normal resistance to mildew, as compared with other varieties grown under comparable cultural conditions at Scappoose, Oregon.

Growth:

*Habit.*—Compact; bushy; much-branched.

*Growth.*—Vigorous.

*Canes.*—Medium heavy.

*Main stems.*—Color—near Spinach Green, Plate 0960/3, page 187. Thorns—several; short to medium length; hooked slightly downward; with long, narrow base. Prickles—few to none; color—dark red. Hairs—none.

*Branches.*—Color—near Maroon, Plate 1030, page 158. Thorns—several; short to medium length; hooked slightly downward; with long, narrow base. Prickles—few to none; color—dark red. Hairs—none.

*New shoots.*—Color—near Maroon, Plate 1030, page 158. Thorns—several; short to medium length; hooked slightly downward; with long, narrow base. Prickles—few to none; color—dark red. Hairs—none.

I claim:

A new and distinct variety of rose plant of the hybrid polyantha class, substantially as herein shown and described, characterized particularly as to novelty by its low-growing, vigorous, much-branched and compact bush habits of growth, by its habit of flowering in moderately large, closely packed clusters, by the unique form and color of its flowers, by its heavy and continuous flowering habit throughout the growing season, by its abundant foliage and even distribution of the same on the stems and branches, and by the unusually persistent deep maroon general color tonality of its new foliage which generally imparts a distinct red cast to the growing plant.

No references cited.